US012653975B2

(12) United States Patent
von Blumenthal et al.

(10) Patent No.: US 12,653,975 B2
(45) Date of Patent: Jun. 16, 2026

(54) VENTILATOR FOR THE MECHANICAL VENTILATION OF A PATIENT

(71) Applicant: Drägerwerk AG & Co. KGaA, Lübeck (DE)

(72) Inventors: Tilman von Blumenthal, Lübeck (DE); Michael Bender, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1004 days.

(21) Appl. No.: 17/725,735

(22) Filed: Apr. 21, 2022

(65) Prior Publication Data

US 2022/0339381 A1 Oct. 27, 2022

(30) Foreign Application Priority Data

Apr. 23, 2021 (DE) .......................... 102021110429.7

(51) Int. Cl.
*A61M 16/00* (2006.01)

(52) U.S. Cl.
CPC ...... *A61M 16/024* (2017.08); *A61M 16/0003* (2014.02); *A61M 2016/0018* (2013.01); *A61M 2016/0027* (2013.01); *A61M 2205/52* (2013.01); *A61M 2230/42* (2013.01)

(58) Field of Classification Search
CPC ................ A61M 16/00; A61M 16/024; A61M 16/0003; A61M 2205/3334; A61M 2205/52; A61M 2016/3334; A61M 2016/0039; A61M 2016/0042
See application file for complete search history.

(56) References Cited

U.S. PATENT DOCUMENTS

2007/0221224 A1* 9/2007 Pittman ............. A61M 16/0069
128/203.14
2008/0283060 A1* 11/2008 Bassin .................. A61M 16/06
128/204.23

(Continued)

FOREIGN PATENT DOCUMENTS

CN 112295070 A 2/2021
DE 69623400 T2 4/2003

(Continued)

*Primary Examiner* — Brandy S Lee
*Assistant Examiner* — Rohan Patel
(74) *Attorney, Agent, or Firm* — McGlew and Tuttle, P.C.

(57) ABSTRACT

A ventilator (100), for mechanical ventilation of a patient (102), includes a sensor unit that measures a course profile (114) of gas flow-dependent measured values (115) in a ventilation circuit (105) of the ventilator and outputs a corresponding sensor signal (116). A plurality of ventilation parameters (122) of a provided ventilation mode, stored in a memory unit (120), indicate an inspiration time (124) of the ventilation currently provided and a subsequent expiration time (126) for a corresponding breathing cycle. A processing unit (130) is configured to receive the sensor signal, to determine at least one current end-expiratory gas flow (132) based on the course profile and to adjust a ratio (136), between the inspiration time and the expiration time, for the current ventilation mode depending on a comparison between the determined current end expiratory gas flow and a lower threshold value (134) and/or an upper threshold value (135).

18 Claims, 5 Drawing Sheets

(56)                    References Cited

U.S. PATENT DOCUMENTS

| | | | | |
|---|---|---|---|---|
| 2013/0255687 A1 * | 10/2013 | Rahlf | ................. | A61M 16/024 |
| | | | | 128/204.26 |
| 2015/0013674 A1 * | 1/2015 | Doyle | ................. | A61B 5/0816 |
| | | | | 128/202.22 |
| 2015/0273172 A1 * | 10/2015 | Pessala | ............ | A61M 16/0069 |
| | | | | 128/203.12 |
| 2016/0136370 A1 * | 5/2016 | Heesch | .............. | A61M 16/024 |
| | | | | 128/204.23 |
| 2019/0134331 A1 | 5/2019 | Meyer et al. | | |

FOREIGN PATENT DOCUMENTS

| | | | | | |
|---|---|---|---|---|---|
| DE | 102018003026 A1 | 10/2019 | | |
| EP | 0127905 A2 | 12/1984 | | |
| EP | 1961378 A1 | 8/2008 | | |
| EP | 3061481 A1 | 8/2016 | | |
| EP | 3769668 A1 | 1/2021 | | |
| FR | 3035592 A1 * | 11/2016 | .......... | G09B 23/288 |
| JP | S57195465 A | 12/1982 | | |
| JP | H0924099 A * | 1/1997 | .......... | A61M 16/024 |
| WO | WO-2016067619 A1 * | 5/2016 | .......... | A61M 16/024 |

* cited by examiner

VENTILATOR FOR THE MECHANICAL VENTILATION OF A PATIENT

CROSS REFERENCE TO RELATED APPLICATIONS

This application claims the benefit of priority under 35 U.S.C. § 119 of German Application 10 2021 110 429.7, filed Apr. 23, 2021, the entire contents of which are incorporated herein by reference.

TECHNICAL FIELD

The present invention relates to a ventilator for mechanical ventilation of a patient. Furthermore, the invention relates to a process for operating a ventilator for mechanical ventilation of a patient.

TECHNICAL BACKGROUND

Ventilators with preset ventilation pressure curves for mechanical ventilation of patients are well known. Depending on the patient's condition, ventilation parameters can be set, such as the positive end-expiratory pressure (PEEP), the mean ventilation pressure, the tidal volume, the respiratory rate and the like.

In order to carry out ventilation in an automated or partially automated manner, it is known that a gas flow and/or a gas flow-dependent measured value must be measured at regular time intervals via at least one sensor. This allows the gas flow to be monitored during an inspiration time and during an expiration time of the corresponding breathing cycle.

SUMMARY

An object of the present invention is to provide an improved ventilator, in particular a ventilator with particularly efficient and patient-friendly ventilation.

According to the invention, a ventilator for mechanical ventilation of a patient is provided for solving this task, with at least a sensor unit, a memory unit and a processing unit.

The at least one sensor unit (comprising one or more sensors) is configured to measure a course profile (a progression) of gas flow-dependent measured values, in particular gas flows, in the ventilation circuit of the ventilator and to output a corresponding sensor signal.

A plurality of ventilation parameters of a currently provided ventilation mode are stored in the memory unit. These stored ventilation parameters indicate at least an inspiration time of the ventilation currently provided by the ventilator and a subsequent expiration time for a corresponding breathing cycle. A breathing cycle is known to be formed by a combination of inspiration time and subsequent expiration time.

The processing unit is configured to receive the sensor signal and to determine at least one current end-expiratory gas flow based on the course of the gas flow-dependent measured values, wherein the processing unit is further configured to adjust a ratio between inspiration time and expiration time for the currently provided ventilation mode for ventilating the patient depending on a comparison between the determined current end-expiratory gas flow and a lower threshold value and/or an upper threshold value, wherein the duration of the corresponding respiratory cycle remains essentially constant—substantially constant.

In the context of the invention, it was recognized that a phase of no expiratory gas flow or low expiratory gas flow results in breathing gas being delivered to the patient unnecessarily rapidly during the inspiratory time. Thus, the expiratory time can be shortened by such a phase of low gas flow to extend the inspiratory time and thereby minimize a gradient of inspiratory gas flow. This is particularly advantageous in view of the fact that ventilation with a low inspiratory gas flow gradient is particularly gentle on the patient.

Alternatively or additionally, the relationship between inspiration time and expiration time can be changed according to the invention, particularly in patients with chronic obstructive disease, by increasing the expiration time if the end-expiratory gas flow is above the upper threshold value. This allows exhalation to be as natural as possible and the subsequent pressure gradient during the inspiratory time is usually not a problem for the corresponding patient group.

A further advantage of the ventilator according to the invention is its ease of implementation. The change in the ratio between inspiration time and expiration time can be implemented as a pure software solution for adapting existing ventilators. This makes it possible to implement the invention in a particularly cost-effective manner.

In view of a large number of ventilation modes for ventilators established on the market, the invention can advantageously be applied to a large number of different ventilation modes, since there is usually an inspiratory time and an expiratory time during ventilation by a ventilator. A ventilation mode is to be understood as meaning a mode of the ventilator that controls, in a mode-specific manner, the ventilation of the patient via the control or regulation of corresponding ventilation parameters.

The course of the gas flow-dependent measured values is a time-dependent course, which describes continuously or in discrete time steps a development of these gas flow-dependent measured values over time.

The ratio between inspiration time and expiration time is, for example, a quotient of inspiration time and expiration time, which is adjusted by changing the inspiration time and/or by changing the expiration time. Preferably, the sum of inspiration time and expiration time, i.e., the duration of a breathing cycle, is preferably kept essentially constant according to a predetermined breathing rate.

The units of the ventilator according to the invention are preferably arranged at least partially spatially separated from each other. For example, the sensor unit is arranged in the ventilation circuit of the ventilator. The ventilation circuit carries the breathing gas (respiratory gas) to the patient and back to the ventilator. The memory unit and the processing unit are preferably arranged in a central housing of the ventilator and are particularly preferably controlled by a common processor. The units are separated from each other at least at the software level.

The lower threshold value and the upper threshold value can be predetermined stored values for the end expiratory gas flow or a system variable correlated therewith. Alternatively or additionally, at least one of the threshold values can be continuously redetermined using currently determined values, such as the gas flow-dependent measured values.

Preferred embodiments of the ventilator according to the invention are described below.

In a particularly preferred embodiment, the processing unit is configured to shorten the expiration time if the current end-expiratory gas flow is below the lower threshold value. In this case, the current end-expiratory gas flow is so low that, from a physiological point of view, a next inspiration phase could have started earlier. Therefore, according to the invention, in this embodiment, the ventilator will shorten the expiratory time in the context of the next breathing cycle. Particularly preferably, the predetermined breathing rate is maintained in this case, so that the shortening of the expiration time leads to a corresponding lengthening of the inspiration time. Particularly preferably, the tidal volume is also kept constant, so that a particularly low pressure gradient, i.e. a particularly low gas flow gradient, and thus particularly gentle ventilation of the patient is possible during the now longer inspiration time.

In a particularly advantageous variant of the preceding embodiment, the processing unit provides a time control in which the current end-expiratory gas flow acts as the measured variable of the time control and the inspiration time acts as the manipulated (control) variable of the time control, and wherein the lower threshold value represents a setpoint value of the measured variable. This type of control can be used to ensure particularly reliably that the duration of the inspiration time is adjusted in accordance with the invention in such a way that the end expiratory gas flow levels off in the range of the lower threshold value. The end-expiratory gas flow leads directly to an intrinsic end-expiratory gas pressure (intrinsic PEEP), to which the pressure is leveled in this variant. Since the pressure is essentially quadratically dependent on the gas flow, a low lower threshold value for the gas flow should thereby lead to an essentially zero (vanishing) intrinsic PEEP. Particularly preferably, together with changing the inspiratory time, the expiratory time is also changed, so that the sum of inspiratory time and expiratory time, i.e. the duration of a breathing cycle, remains constant. The provision of such control elements within a control device is known to the person skilled in the art and will therefore not be explained in detail below. In particular, it is known how such a control can be carried out without a strong oscillation behavior of the parameters and thus an impairment of the patient's ventilation.

In a variant of the described embodiments that is alternative or additional to the preceding variant, the processing unit is configured to extend (lengthen) the expiration time if the current end-expiratory gas flow is above the upper threshold value. In this variant of the embodiment, a gas flow range between the lower threshold value and the upper threshold value is predetermined, in which the end-expiratory gas flow should lie. If the end-expiratory gas flow is outside this range, the expiration time is extended or shortened such that an end-expiratory gas flow within this range is again achieved. If the end-inspiratory gas flow is above the upper threshold value, an extension of the expiration time ensures that the end-inspiratory gas flow decreases and consequently falls below the upper threshold value even if the expiration time is sufficiently extended. Accordingly, the upper threshold value is basically above the lower threshold value according to the invention. Such a lengthening of the expiration time can be advantageous, for example, in patients with chronic obstructive disease who have to exhale for a comparatively long period before inhalation can begin again. In these patients, the resulting increased pressure gradient during the inspiratory time is usually not detrimental to patient well-being.

According to the invention, the processing unit of the ventilator is configured to always adjust the expiration time and the inspiration time in such a way that the duration of the corresponding breathing cycle remains essentially constant. This advantageously ensures that a preferably predetermined breathing frequency of the ventilation is kept essentially constant by the ventilator according to the invention.

Since the breathing rate is a particularly relevant predefined ventilation parameter of almost any ventilation mode, maintaining a duration of the breathing cycle is particularly advantageous in the context of this embodiment.

In a further embodiment of the ventilator according to the invention, the lower threshold value and/or the upper threshold value are dependent on the measured course of the gas flow-dependent measured values. Due to the dependence on the measured course, the two threshold values in this embodiment are particularly advantageously at least partially dependent on the ventilation characteristics of the specific patient. Particularly preferably, the lower threshold value and/or the upper threshold value are dependent on a maximum gas flow, in particular a maximum expiratory gas flow. For example, the lower threshold value can be between 0.1% and 5%, preferably between 0.5% and 3%, in particular at 2% of the maximum expiratory gas flow. The expiratory gas flow is basically that gas flow of a breathing gas which the patient has exhaled during the expiratory period, whereas the inspiratory gas flow is that gas flow of a breathing gas (respiratory gas) which the patient inhales during the inspiratory period. Thus, the maximum expiratory gas flow is determined from at least one of the gas flow-dependent measured values from the measured history.

In an advantageous embodiment, the processing unit is further configured to adjust an increase in a gas pressure of the breathing gas at the start of the inspiration time and/or a maximum pressure of the breathing gas during the inspiration time as a function of the adjustment of the inspiration time. By adjusting the increase of the gas pressure and/or the maximum pressure, the provided ventilation characteristic is advantageously adapted to the adjusted inspiration time. For example, a longer expiration time may result in the maximum pressure being reduced so that ventilation during the inspiration time is gentler on the patient. Alternatively or additionally, a longer inspiratory time may have the effect of reducing the increase in gas pressure, in particular the increase in gas pressure at the beginning of the inspiratory time. This reduces the gradient of the gas pressure and thus the gradient of the gas flow, which is known to make ventilation by the ventilator more comfortable for the patient. Consequently, in this embodiment, ventilation parameters are particularly advantageously adapted to the current state of the patient's ventilation in order to enable particularly effective and preferably particularly patient-friendly ventilation.

In an advantageous embodiment, the processing unit is further configured to determine a current end-inspiratory gas flow over the course of the gas flow-dependent measured values and, depending on the current end-inspiratory gas flow, to adjust a ramp duration of the increase in the gas pressure of the breathing gas at the start of the inspiration time. The ramp duration is the time interval at the beginning of the inspiration time at which the inspiratory gas flow to the patient is increased linearly over time, i.e. in a ramped manner, up to a maximum inspiratory gas flow. By evaluating the current end-inspiratory gas flow, a further characteristic value from the measured course of the gas flow-dependent measured values is advantageously used to improve ventilation by the ventilator according to the invention. The end-inspiratory gas flow can be used to determine whether there is still a time range remaining at the end of the expiration time in which no supply of breathing gas to the patient takes place before the expiration time of the corresponding respiratory cycle begins. In a preferred variant of this embodiment, the processing unit is configured to extend the ramp duration if the current end-inspiratory gas flow is below a lower inspiratory threshold value, and at the same time to shorten a remaining plateau duration of the inspiratory time so that the inspiratory time, i.e. the total inspiratory time, is independent of the end-inspiratory gas flow. This can ensure that during the inspiratory time the breathing gas to be delivered to the patient, preferably with a predetermined breathing gas volume, can be provided as gently as possible to the patient. The lower inspiratory threshold value can be a fixed predetermined value. Alternatively or additionally, the inspiratory threshold value can be dependent on the measured course of the gas flow-dependent measured values. By depending on the measured course, the threshold value in this embodiment is particularly advantageously at least partially dependent on the ventilation characteristics of the specific patient. Particularly preferably, the lower inspiratory threshold value is dependent on a maximum gas flow, in particular a maximum inspiratory gas flow. For example, the lower inspiratory threshold value can be between 0.1% and 5%, preferably between 0.5% and 3%, in particular at 2% of the maximum inspiratory gas flow.

In a particularly preferred variant of the preceding embodiment, the processing unit provides a ramp control in which the current end-inspiratory gas flow acts as the measured variable of the ramp control and the ramp duration acts as the manipulated control variable of the ramp control, and wherein the lower inspiratory threshold value represents a setpoint (target) value of the measured variable. In this variant, the ramp duration can be used to advantageously ensure that the inspiratory gas flow levels off in the range of the lower inspiratory threshold value. Decreasing the ramp duration reduces the end-inspiratory gas flow, whereas increasing the ramp duration increases the end-inspiratory gas flow.

In an alternative or additional variant to the previous variant, the processing unit is configured to shorten the ramp duration if the current end-inspiratory gas flow is above an upper inspiratory threshold value and, at the same time, to extend a remaining plateau duration of the inspiratory time so that the inspiratory time is independent of the end-inspiratory gas flow. In this embodiment, the ventilator according to the invention is configured to define a range for the inspiratory gas flow in which the ventilator is operated via the predetermined upper inspiratory threshold value and the predetermined lower inspiratory threshold value by controlling the ramp duration.

The predetermined upper inspiratory threshold value and/or the predetermined lower inspiratory threshold value are preferably dependent on the measured course of the gas flow-dependent measured values. Particularly preferably, the lower inspiratory threshold value and/or the upper inspiratory threshold value is dependent on a maximum inspiratory gas flow during the inspiration time of the provided ventilation determined from the gas flow-dependent measured values.

In a particularly preferred embodiment, the processing unit is further configured to only lengthen the expiration time and/or to only lengthen the ramp duration at a constant maximum pressure if, as a result, a mean ventilation pressure over the corresponding breathing cycle is not below a predetermined lower mean pressure threshold value. In this embodiment, it is advantageously ensured that the mean pressure does not fall below the predetermined lower mean pressure threshold value. This is particularly advantageous because the lower mean pressure threshold value is a particularly relevant parameter when ventilating a patient, so that the ventilator should reliably ensure that the mean pressure actually present at the patient as a result of adjusting the expiration time and/or the ramp duration is always above this threshold value. Thus, in this embodiment, the ventilator according to the invention allows, in addition to patient-gentle ventilation, compliance with the specified lower mean pressure threshold value by adjusting the expiration time and/or the ramp duration and thus ensures that the patient's ventilation is particularly patient-friendly (gentle). A determination of the mean ventilation pressure is common in ventilators known to the skilled person and typically takes place by summing up ventilation pressures over time.

In a further embodiment, the ventilator according to the invention further comprises a user interface configured to receive a user input. The user input indicates, for example, a range for the ratio between inspiration time and expiration time that is adjustable by the ventilator. The ratio between inspiration time and expiration time is preferably between a ratio of 1 to 1 and a ratio of 1 to 5, such as between a ratio of 1 to 1 in a ratio of 1 to 3. The user input may alternatively or additionally indicate the ventilation mode to be used. Alternatively or additionally, the user input may indicate a ventilation parameter to be stored, such as a respiratory rate, a digital volume, a maximum pressure of the breathing gas during the inspiration time, an increase in gas pressure at the beginning of the inspiration time, the lower end expiratory gas flow threshold value, the lower mean pressure threshold value, or the like.

According to a further aspect of the invention, a process for operating a ventilator for mechanical ventilation of a patient is provided for solving the above problem, comprising the steps:

measuring a course profile (progression) of gas flow-dependent measured values in the ventilation circuit of the ventilator and outputting a corresponding sensor signal;
    storing a plurality of ventilation parameters of a currently provided ventilation mode, these stored ventilation parameters indicating at least an inspiration time of the ventilation currently provided by the ventilator and a subsequent expiration time for a corresponding breathing cycle;
    receiving the sensor signal and determining at least one current end-expiratory gas flow based on the history (course profile) of the gas flow-dependent measured values; and
    adjusting a ratio between inspiration time and expiration time for the currently provided ventilation mode for ventilating the patient depending on a comparison between the determined current end-expiratory gas flow and a lower threshold value and/or an upper threshold value.

The process according to the invention is carried out by the ventilator according to the invention and therefore comprises all advantages mentioned in the context of the ventilator. Furthermore, the process according to the invention can be supplemented by features corresponding to the described embodiments of the ventilator according to the invention.

Particularly advantageously, the process according to the invention allows dynamic adjustment of the ratio between inspiration time and expiration time. In this way, it can be taken into account that the current end expiratory gas flow is particularly high or particularly low, so that the inspiration time and/or the expiration time can be adjusted accordingly to enable particularly patient-friendly ventilation during the inspiration time and at the same time to avoid phases without inspiratory and expiratory gas flow.

The steps of the process according to the invention can be carried out in a sequence other than that shown. In particular, the storage of the plurality of ventilation parameters can also be carried out before the measurement of the course of gas flow-dependent measured values.

Preferably, less than 20 seconds, in particular less than 10 seconds, especially preferably less than 2 seconds, elapse between the measurement of the course of the gas flow-dependent measured values and the corresponding adjustment of the ratio between inspiration time and expiration time. In this way, the inspiratory time and expiratory time can be adjusted essentially in real time, so that the patient's ventilation can be adapted particularly quickly to the current state of the patient-specific respiration.

In one embodiment of the process according to the invention, an average is taken over a number of past end-expiratory gas flows, such as the last two end-expiratory gas flows, in order to compare the average value with the lower threshold value and/or the upper threshold value. In this embodiment, the comparison is performed as a function of the current end-expiratory gas flow in that the determined averaged value is a function of the current end-expiratory gas flow. In an alternative embodiment, the ratio between inspiration time and expiration time is adjusted solely based on the last determined current end-expiratory gas flow.

The invention will now be explained in more detail with reference to advantageous examples of embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
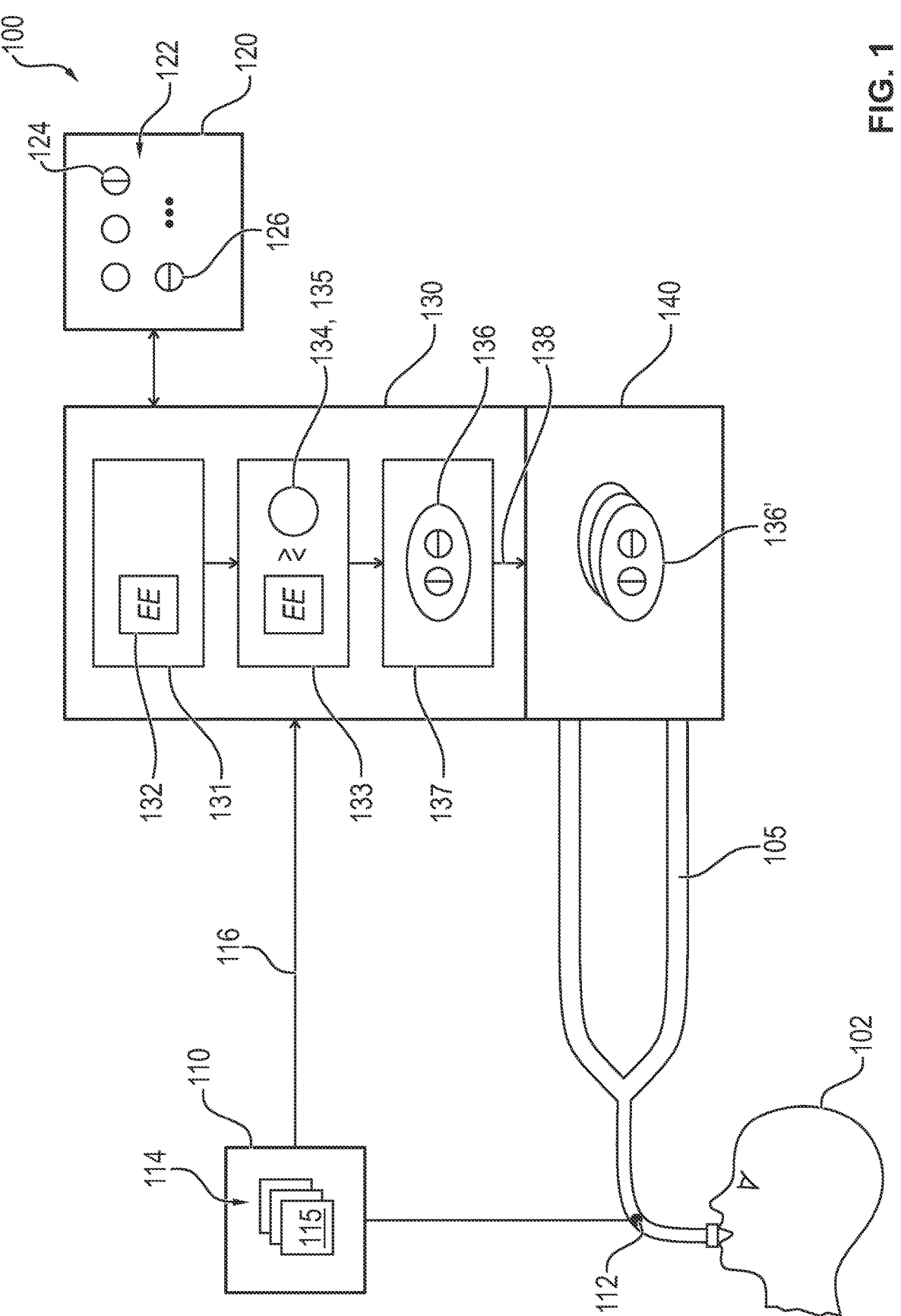
FIG. 1 is a schematic view of an exemplary embodiment of a ventilator according to the invention.

Referring to the drawings, FIG. 1 shows a schematic diagram of an embodiment of a ventilator 100 according to the invention.

The ventilator 100 is configured to mechanically ventilate a patient 102. In this regard, the ventilator 100 comprises at least a sensor unit 110, a memory unit 120, and a processing unit 130.

The at least one sensor unit 110 is configured to measure a course profile (progression) 114 of gas flow-dependent measured values 115 in the ventilation circuit 105 of the ventilator 100. For this purpose, the sensor unit 110 in the illustrated embodiment example has a sensor head 112, which is arranged within the ventilation circuit 105, in particular close to a tube located on the patient 102. In addition, the sensor unit 110 is configured to output a corresponding sensor signal 116. In the present case, the gas flow-dependent measured values 115 are a measured gas flow. Alternatively or additionally, in an embodiment example not shown, the gas pressure is measured as a gas flow-dependent measured value.

The memory unit 120 includes a memory in which a plurality of ventilation parameters 122 of a currently provided ventilation mode of the ventilator 100 are stored. The plurality of stored ventilation parameters 122 indicate at least an inspiration time 124 of the ventilation currently provided by the ventilator 100 and a subsequent expiration time 126 for a corresponding breathing cycle. In the illustrated embodiment, the memory unit 120 stores at least the inspiration time 124, the subsequent expiration time 126, a vital volume to be provided, a respiratory rate, and a maximum pressure during inspiration. For this purpose, the memory unit 120 may be connected to a user interface for entering ventilation parameters and/or to a control unit 140 of the ventilator 100 for presetting the current ventilation parameters and/or to a network, in particular a hospital network, for providing the ventilation parameters to be used. For reasons of clarity, such a connection corresponding to one of these variants is not shown in FIG. 1.

The processing unit 130 is configured to receive the sensor signal 116 and to determine at least one current end-expiratory (EE) gas flow 132 based on the course profile 114 of the gas flow-dependent measured values 115. The determination of the current end-expiratory gas flow 132 takes place within a first module 131 in the illustrated embodiment example. a second module 133 of the processing unit 130 connected thereto is further configured to adjust a ratio 136 between inspiration time 124 and expiration time 126 for the currently provided ventilation mode for ventilating the patient 102, depending on a comparison between the determined current end-expiratory gas flow 132 and a lower threshold value 134 and/or an upper threshold value 135. The determination of the ratio 136 to be then newly provided is performed in a third module 137 of the processing unit 130, with the three modules 131, 133 and 137 being separated at least at the software level such that different processing steps of a program to be executed represent different modules.

In this case, the processing unit 130 is configured to output that ratio to the control unit 140 of the ventilator 100 through a corresponding internal output 138 from the third module 137. The control unit 140 applies the newly determined ratio 136 by overwriting the previously used ratio 136' between inspiration time 124 and expiration time 126 when ventilating the patient 102.

In the illustrated embodiment, the processing unit 130 is configured to shorten the expiration time 126 if the current end-inspiratory gas flow 132 is below the lower threshold value 134. This advantageously ensures that the inspiration time 124 is as long as possible so that the pressure gradient is as low as possible during ventilation at a constant tidal volume and constant respiratory rate. This makes it possible to provide ventilation that is particularly gentle on the patient.

A too large end-expiratory gas flow correlates with a large intrinsic end-expiratory pressure (intrinsic PEEP), which is also known to be avoided. For this purpose, the processing unit is preferably configured to extend (lengthen) the expiration time 126 if the current end-expiratory gas flow 132 is above the upper threshold value 136.

The ratio between inspiration time 124 and expiration time 126 is always changed in such a way that the duration of the corresponding breathing cycle, i.e. the sum of inspiration time and expiration time, always remains constant. This ensures that a preferably predetermined breathing frequency remains essentially unchanged during the adjustment of the ratio.

In the illustrated embodiment example, the lower threshold value and/or the upper threshold value are dependent on the measured course 114 of the gas flow-dependent measured values 115. Thus, these two threshold values are determined based on the maximum expiratory gas flow during the expiration time 126. Preferably, the lower threshold value is between 0.5% and 5% of the maximum expiratory gas flow, in particular between 1% and 3% of the maximum expiratory gas flow, particularly preferably about 2% of the maximum expiratory gas flow.

Finally, the processing unit 130 is further configured to lengthen (extend) the expiratory time 126 only if, as a result, a mean ventilation pressure over the corresponding breathing cycle is not within a predetermined lower mean pressure threshold value.

In an alternative or complementary embodiment, the processing unit is further configured to adjust a course of the gas flow during the inspiration time 124, for example, by changing the increase of the gas flow and/or by changing a maximum gas flow during the inspiration time 124.

The various units of the ventilator 100 according to the invention may be arranged at least partially in a common housing. In this case, the various units are separated from one another at least at the software level. Communication between these units is cable-based or wireless. Various possibilities for implementing such cable-based or wireless communication are known to the person skilled in the art, so that they will not be discussed in detail below.

Figure 2:
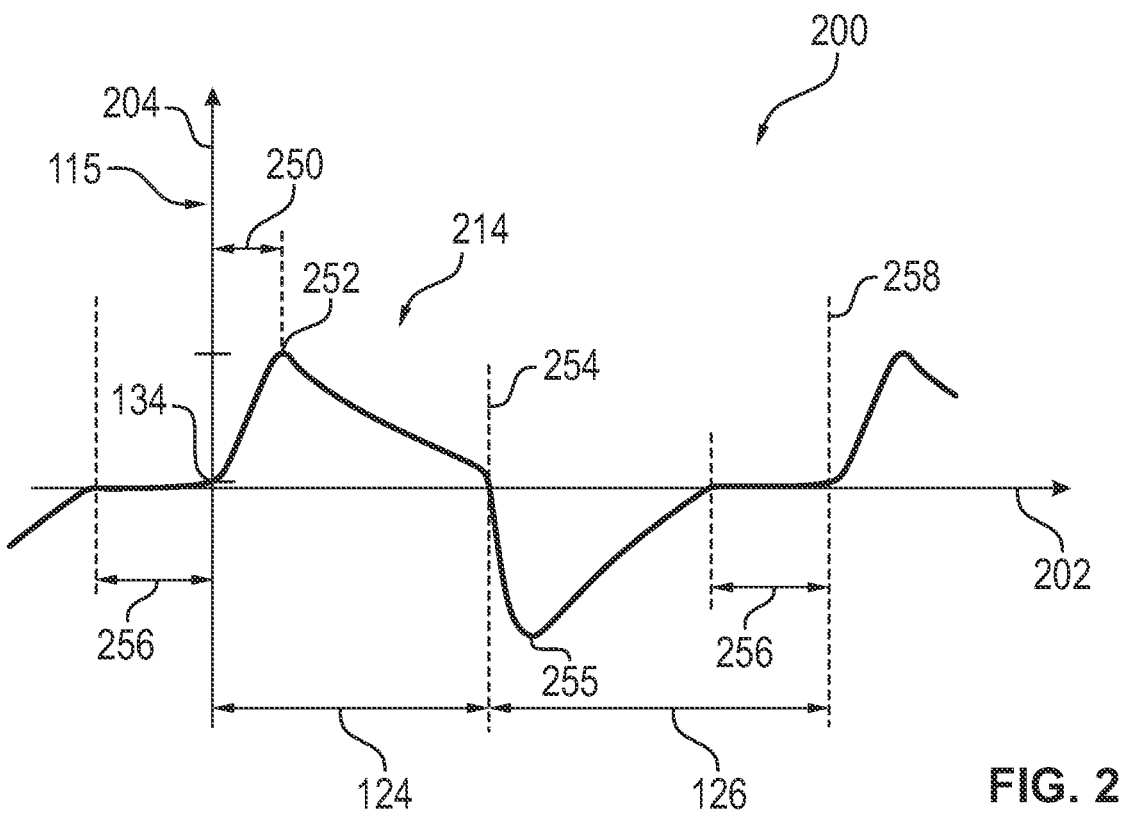
FIG. 2 is a diagram of the course profile of gas flow-dependent measured values before an adjustment of the ratio between inspiration time and expiration time in an embodiment according to the invention.
Figure 3:
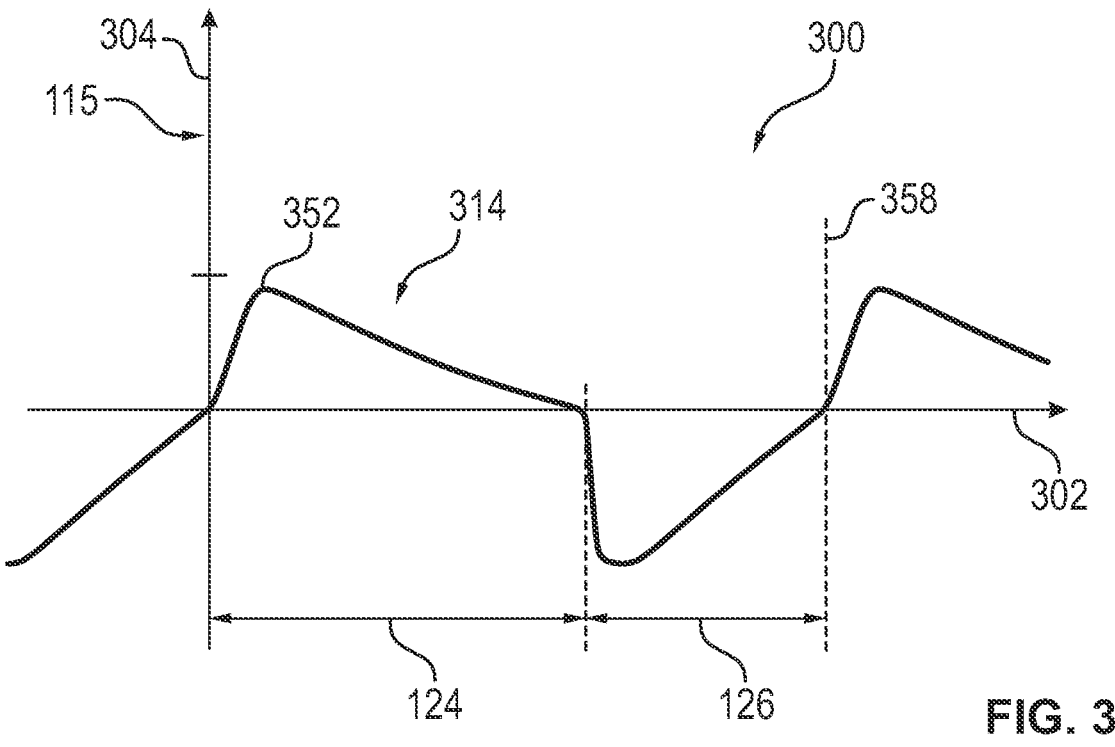
FIG. 3 is a diagram of the course profile of gas flow-dependent measured values after an adjustment of the ratio between inspiration time and expiration time in an embodiment according to the invention.

FIGS. 2 and 3 show a respective diagram 200, 300 of the course 214, 314 of gas flow-dependent measured values 115, before (FIG. 2) and after (FIG. 3) an adjustment of the ratio between inspiration time 124 and expiration time 126 in an embodiment according to the invention.

The diagrams 200, 300 show above the respective X-axis 202, 302 the time represented over slightly more than one respective breathing cycle. The duration of a breathing cycle is between 3 seconds and 12 seconds, in particular between 5 seconds and 10 seconds. At the coordinate origin of the respective diagram 200, 300 lies the beginning of the respective represented breathing cycle.

The gas flow-dependent measured value, i.e. the gas flow in this case, is displayed via the respective Y-axis 204, 304. A displayed marker is at a value of 25 L/min.

The gas flow is positive during the inspiratory time 124 and negative during the expiratory time 126. During the inspiratory time 124, the gas flow increases essentially linearly for a ramp duration 250 before decreasing after a maximum inspiratory gas flow 252. The inspiratory end 254 of the inspiratory time 124 ideally has a positive gas flow near 0 L/min. After the inspiratory end 254, the expiratory time 126 begins, during which the gas flow increases to a maximum expiratory gas flow 255 in the negative direction of the Y-axis, before the gas flow decreases again to a value close to 0 L/min. Before the expiratory time 126 is adjusted according to the invention, there is an extended region 256 in the exemplary course 214 shown in FIG. 2 where there is essentially no gas flow until the next inspiratory time 124 begins again after the expiratory end 258. If ventilation were to continue in this manner, there would be the extended expiratory region 256 in each breathing cycle that does not effectively contribute to the ventilation of the corresponding patient.

According to the invention, therefore, when the course 214 is present, it is determined that a lower threshold value 134 is undershot at the expiratory end 258, so that the relationship between inspiratory time 124 and expiratory time 126 is adjusted. In the illustrated embodiment, the lower threshold value 134 is about 2% of the maximum expiratory gas flow 255.

By falling below this lower threshold value 134, the expiratory time 126 is shortened while the inspiratory time 124 is lengthened, as shown in FIG. 3. The entire respiratory cycle retains its duration, so that the end of expiration 358 is essentially at the same time as the end of expiration 258 of FIG. 2. The course of expiration is identical in FIGS. 2 and 3, except for the fact that the shortening of expiration time 126 eliminates the extended region 256 with no or little gas flow. The course of expiration is essentially dependent on the tidal volume provided and the patient physiology present, and thereby independent of any change in the course 214 of gas flow during inspiration time 124.

The volume of gas to be delivered is delivered over a longer period of time given the extended inspiratory time 124, so that the gradient of the gas flow, i.e. the change per time, is lower and thus more comfortable for the patient. In addition, in the illustrated embodiment, the maximum inspiratory gas flow 352 is less than the maximum inspiratory gas flow 252 of FIG. 2. In another embodiment, depending on the adjustment of the inspiration time, an increase in the gas pressure of the breathing gas at the beginning of the inspiration time and/or a maximum pressure of the breathing gas during the inspiration time is adjusted.

The adjustment of the ratio between inspiration time 124 and expiration time 126 can be provided via a predetermined time control, in which the current end-expiratory gas flow acts as the measured variable of the time control and the inspiration time acts as the manipulated control variable of the time control, and in which the lower threshold value represents a setpoint (target) value of the measured variable. This ensures, for example, that a reduction in the expiration time 126 does not lead to an intrinsic end-expiratory gas pressure (intrinsic PEEP).

The further ventilation parameters to be taken into account during ventilation are known to the person skilled in the art depending on the ventilation mode present. Preferably, at least the respiration rate of the ventilation is preset. Preferably, at least one of the following pressures is also preset: positive end expiratory pressure (PEEP), maximum inspiratory pressure, mean respiratory pressure. If only one of these pressures is predefined, the tidal volume of the ventilation is preferably also a predefined ventilation parameter of the present ventilation mode.

Figure 4:
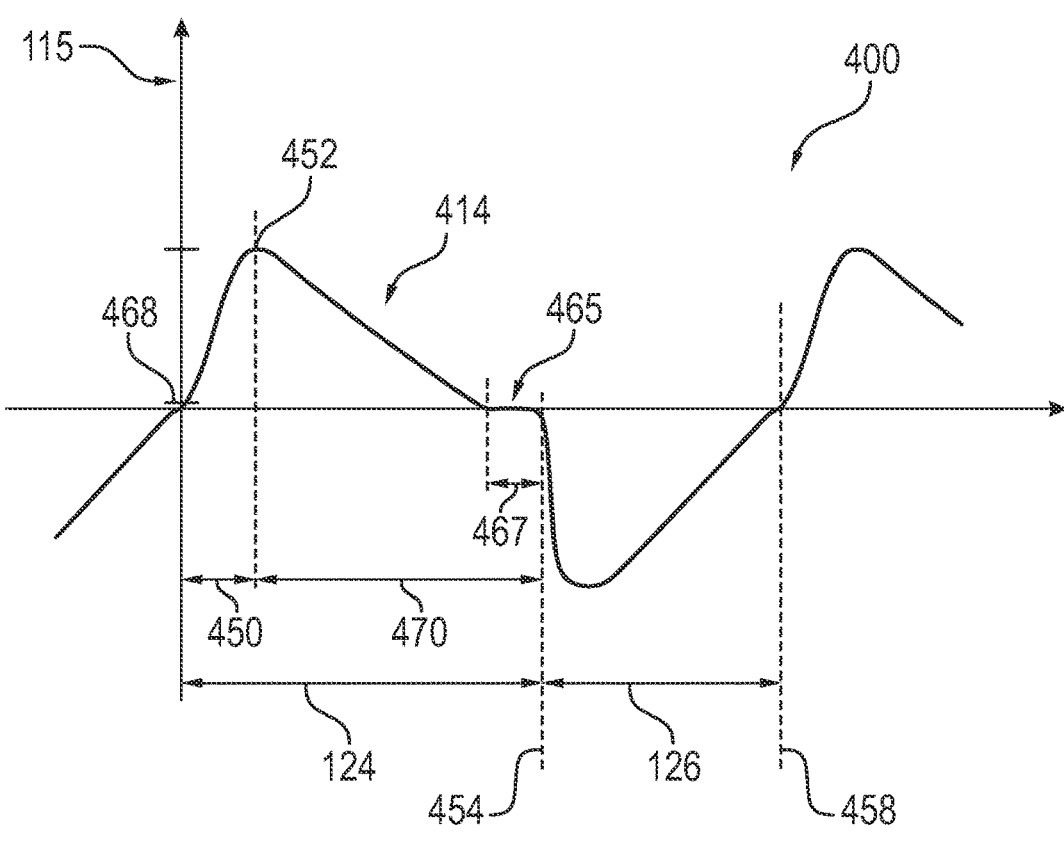
FIG. 4 is a diagram of the course profile of gas flow-dependent measured values before adjusting a ramp duration of an increase in a gas pressure of a breathing gas in an embodiment according to the invention.
Figure 5:
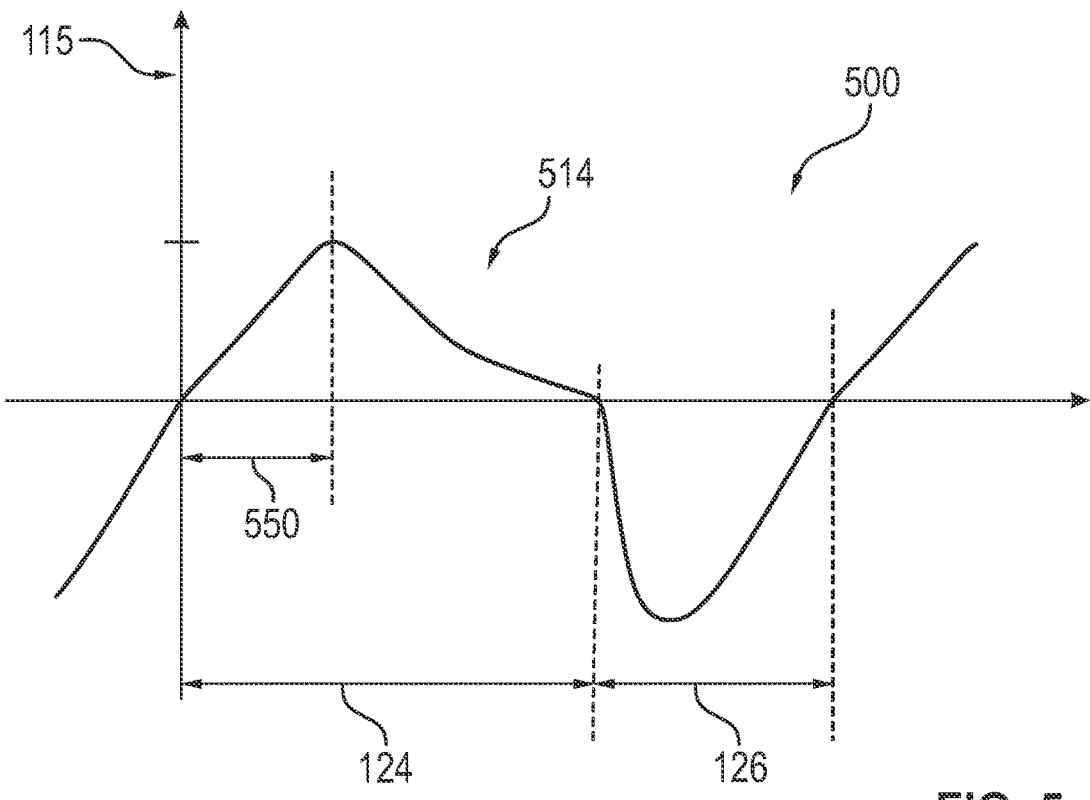
FIG. 5 is a diagram of the course profile of gas flow-dependent measured values after adjusting a ramp duration of an increase in a gas pressure of a breathing gas in an embodiment according to the invention.

FIGS. 4 and 5 show a respective diagram 400, 500 of the course 414, 514 of gas flow-dependent measured values 115, before (FIG. 4) and after (FIG. 5) an adjustment of a ramp duration 540, 550 of an increase of a gas pressure of a breathing gas in an embodiment according to the invention.

The axes of the diagrams 400, 500 are formed identically to the axes from the diagram 200, 300.

In FIG. 4, the curve 414 of gas flow-dependent readings 115 differs from the trajectories of FIGS. 2 and 3 in that an end-inspiratory gas flow 465 over an extended inspiratory range 467 is essentially 0 l/min. In addition to the inspiratory end 454 and expiratory end 458, the time of the maximum inspiratory gas flow 452 is indicated, which is the end of the ramp duration 450.

The ventilator according to the invention determines that the end-inspiratory gas flow 465 is above a lower inspiratory threshold value 468 and, therefore, an extension of the ramp duration 450 must occur while maintaining the length of the inspiratory time 124. Here, the plateau duration 470, which is the remaining time of the inspiratory time 124, is shortened. The term plateau duration is derived for this time interval because a pressure within the Y-piece remains constant during this time range, while the remaining positive gas flow travels directly to the patient's lungs. As a result, a pressure plateau is known to exist in this time range for a pressure sensor typically located in the area of the Y-piece.

The resulting curve 514 is shown in FIG. 5. The ramp duration 550 is approximately twice as long as the ramp duration 540 from FIG. 4, whereas the course 514 remains essentially unchanged during the expiration time 126. The longer ramp duration 550 is used to reduce the increase in gas flow and thus to gently ventilate the corresponding patient.

The ventilator from this embodiment would also reduce the ramp duration accordingly at an end-inspiratory gas flow above an upper inspiratory threshold value.

The suitable adjustment of the ramp duration and/or the inspiratory time and/or the expiratory time is realized by an iterative adjustment by predetermined time increments. After each adjustment process, the influence on the corresponding course profile of the measured values is taken into account in order to control the further adjustment. Such a procedure is generally known in the field of control engineering, so that the possibilities of control engineering implementation will not be discussed in detail below.

Figure 6:
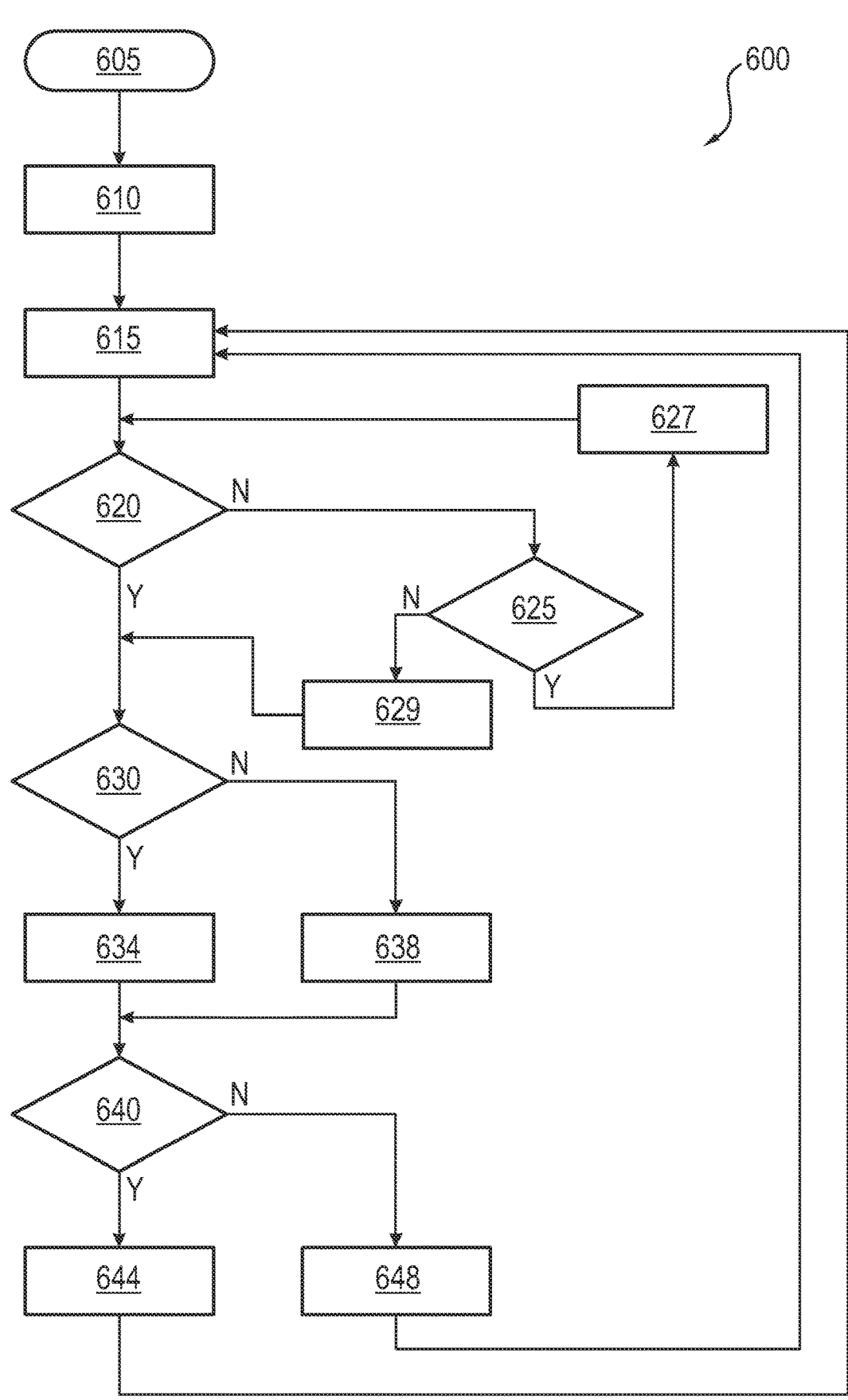
FIG. 6 is a flow diagram of a control of ventilation parameters in an embodiment according to the invention.

FIG. 6 shows a flow diagram of a control 600 of ventilation parameters in an embodiment according to the invention.

Control 600 illustrates an example embodiment of the steps of the ventilator according to the invention when adjusting the inspiration time and ramp duration.

After the start 605 of the control according to the invention, the input and storage of the plurality of ventilation parameters is performed in step 610, after which the ventilation of the patient is started in step 615.

During ventilation in this embodiment example, it is advantageously always checked in step 620 whether the average ventilation pressure over the corresponding breathing cycle is above a predefined lower average pressure threshold value. The mean ventilation pressure is calculated, for example, by summing the measured gas flow-dependent measured values, for example the measured gas pressures, with a corresponding scaling. Alternatively or additionally, the mean ventilation pressure MAP can be calculated approximately by the following calculation rule:

$$MAP = PEEP + (TI - \frac{1}{2} * TRamp) * RR * P.$$

Here, TI is the inspiratory time, which results, for example, from the ratio between inspiratory time and expiratory time and the given respiratory rate RR. In addition, TRamp is the ramp duration and P is the inspiratory pressure jump, which results from a quotient of tidal volume and lung capacity.

If it is determined in step 620 that the average ventilation pressure is above the lower average pressure threshold value, control 600 continues with step 630. If the mean ventilation pressure is below the lower mean pressure threshold value, step 625 checks whether the current ramp duration is greater than a predetermined minimum ramp duration. If the ramp duration is greater than the predetermined minimum ramp duration, step 627 incrementally reduces the ramp duration and repeats step 620. If the ramp duration is less than or equal to the minimum ramp duration, the inspiration time is increased in step 629 to increase the mean ventilation pressure and step 630 is continued.

In step 630, it is checked whether the end expiratory gas flow is greater than 2% of the maximum expiratory gas flow. If the end expiratory gas flow is greater than 2% of the maximum expiratory gas flow, the expiratory time is increased in step 634 while the sum of the inspiratory time and expiratory time is held constant until the end expiratory gas flow is essentially 2% of the maximum expiratory gas flow and/or the mean ventilation pressure is equal to the lower mean pressure threshold value. If the end expiratory gas flow is greater than 2% of the maximum expiratory gas flow, in step 638, the expiratory time is shortened until the end expiratory gas flow is essentially 2% of the maximum expiratory gas flow.

Then, step 640 is performed to check whether the end-inspiratory gas flow is greater than 2% of the maximum inspiratory gas flow. If the end-inspiratory gas flow is greater than 2% of the maximum inspiratory gas flow, the ramp duration is reduced in step 644 until the end-inspiratory gas flow is essentially 2% of the maximum inspiratory gas flow or the ramp duration is essentially equal to the minimum ramp duration. If the end-inspiratory gas flow is less than 2% of the maximum inspiratory gas flow, the ramp duration is increased in step 648 until the end-inspiratory gas flow is essentially 2% of the maximum inspiratory gas flow or the mean ventilation pressure is essentially equal to the lower mean pressure threshold value.

After performing step 644 or step 648, the steps beginning with performing ventilation 615 are performed again.

In this embodiment example, all aspects of the control of the ventilator according to the invention are explained. In alternative embodiments, only the control of the inspiration time or only a combination of the control of the inspiration time and the ramp or only a combination of the control of the inspiration time and the mean ventilation pressure is performed.

The structure of the control 600 essentially visualizes the iterative nature of the control according to the invention. Thereby, the incremental change of a value occurs each time a corresponding step of this control 600 is passed. Suitable starting conditions for the ventilation are known from medical practice and are therefore not presented in the following.

Figure 7:
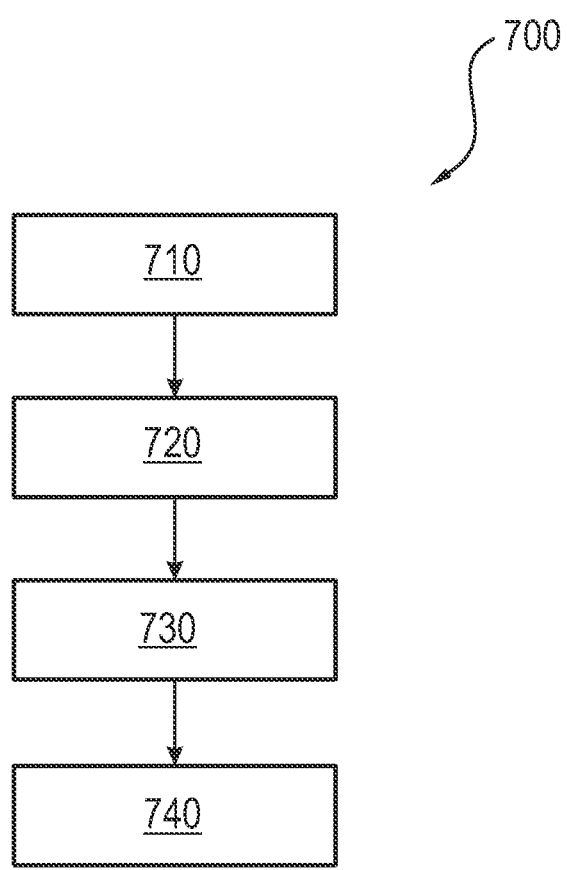
FIG. 7 is a flowchart of an embodiment of a process according to a further aspect of the invention.

FIG. 7 shows a flow diagram of an embodiment of a process 700 according to a further aspect of the invention. Compared with the arrangement shown in FIG. 6, the process 700 represents a superordinate sequence of process steps according to the invention. It is clear to the person skilled in the art from the following explanation that individual process steps of the process 700 may comprise several stages of the control 600 explained in the context of FIG. 6.

The process 700 according to the invention is designed for operating a ventilator for mechanical ventilation of a patient. For this purpose, the process 700 has the steps shown below.

A first step 710 includes measuring a course profile (a history) of gas flow-dependent measurements in the ventilator circuit of the ventilator and outputting a corresponding sensor signal.

A subsequent step 720 comprises storing a plurality of ventilation parameters of a currently provided ventilation mode, these stored ventilation parameters indicating at least an inspiration time of ventilation currently provided by the ventilator and a subsequent expiration time for a corresponding breathing cycle.

A further step 730 comprises receiving the sensor signal and determining at least one current end-expiratory gas flow based on the course of the gas flow-dependent measured values.

A final step 740 comprises adjusting a ratio between inspiration time and expiration time for the currently provided ventilation mode for ventilating the patient depending on a comparison between the determined current end-expiratory gas flow and a lower threshold value and/or an upper threshold value.

The sequence of the process steps 710 and 720 can change. Thus, the storage of the plurality of ventilation parameters can already take place with the provision of the ventilation device, but can also take place again during the execution of the process by changing ventilation parameters.

The further steps 730 and 740 are carried out after the two initial steps 710 and 720. The determination of the current end expiratory gas flow according to step 730 always takes place before the adjustment of the ratio between inspiration time and expiration time according to step 730.

Preferably, steps 730 and 740 are performed at least almost in real time, so that the measured values for a breathing cycle can already be taken into account when changing the ratio between inspiration time and expiration time of the subsequent breathing cycle. In an alternative or supplementary embodiment example, the adjustment of the ratio between inspiration time and expiration time is performed based on a number of measured values from previous breathing cycles, in particular based on the last two breathing cycles. Taking into account previous breathing cycles can improve a reliability of the ventilator according to the invention, since, for example, measurement errors can be concluded from a comparison between the current breathing cycle and the past breathing cycle if the deviation is particularly large. For example, a deviation above a deviation threshold value can lead to the current measured values not being used for adjusting the ratio between inspiration time and expiration time.

The steps of the process 700 of the invention may be performed multiple times within the process. For example, multiple current end-expiratory gas flows may be determined according to step 730 before adjusting the ratio of inspiratory time to expiratory time according to step 740.

Preferably, at least parts of the process according to the invention, such as the measurement according to step 710, the determination of the current end-expiratory gas flow according to step 730 and the adjustment according to 740, are carried out again for each breathing cycle. According to the invention, the adjustment according to step 740 is only carried out if the comparison between the determined current end-expiratory gas flow and the corresponding threshold value according to a stored regulation indicates this.

The various process steps of the process 700 may be executed at a common location, for example by a common device. In this case, the execution of the individual steps is separated from each other, at least at the software level, for example by a common processor. Alternatively, the process 700 may be executed at least partially at different locations.

While specific embodiments of the invention have been shown and described in detail to illustrate the application of the principles of the invention, it will be understood that the invention may be embodied otherwise without departing from such principles.

LIST OF REFERENCE CHARACTERS

100 Ventilator
102 Patient
105 Ventilation circuit
110 Sensor unit
112 Sensor head
114, 214, 314, 414, 514 Course profile (progression of measured values)
115 Gas flow dependent measured value
116 Sensor signal
120 Memory unit
122 Ventilation parameters
124 Inspiration Time
126 Expiration time
130 Processing unit
131 First module
132 end expiratory gas flow
133 second module
134 lower threshold value
135 Upper threshold value
136 Relationship between inspiration and expiration time
136' past relationship back ratio
137 third module
138 internal output
140 Control unit
200, 300, 400, 500 Diagram
202, 302 X-axis
204, 304 Y-axis
250, 450, 550 Ramp duration
252, 352, 452 Maximum inspiratory gas flow
254, 454 Inspirational end
255 maximum expiratory gas flow
256 extended expiratory range
258, 358, 458 Expiratory end
465 end-inspiratory gas flow
467 extended inspiratory range
468 lower inspiratory threshold value
470 Plateau duration
600 Control
605, 610, 615, 620, 625, control steps
627, 629, 630, 634, 638,
640, 644, 648
700 Process
710, 720, 730, 740 Process steps

What is claimed is:

1. A ventilator for a mechanical ventilation of a patient, the ventilator comprising:
   a sensor unit configured to measure a course profile of gas flow-dependent measured values in a ventilation circuit of the ventilator and to output a corresponding sensor signal;
   a memory unit in which a plurality of ventilation parameters of a currently provided ventilation mode are stored, said stored ventilation parameters indicating at least an inspiration time of the currently provided ventilation mode by the ventilator and a subsequent expiration time for a corresponding breathing cycle;

a processing unit configured:

to receive the sensor signal;

to determine at least one current end-expiratory gas flow based on the course profile of the gas flow-dependent measured values;

to make a comparison between the determined current end-expiratory gas flow and a lower threshold value or an upper threshold value or both a lower threshold value and an upper threshold value;

to adjust a ratio between the inspiration time and the expiration time for the currently provided ventilation mode for ventilating the patient based on the comparison, wherein a duration of the corresponding breathing cycle remains essentially constant; and to adjust, depending on the adjustment of the inspiration time, an increase of a gas pressure of the breathing gas at the beginning of the inspiration time or a maximum pressure of the breathing gas during the inspiration time or both an increase of a gas pressure of the breathing gas at the beginning of the inspiration time and a maximum pressure of the breathing gas during the inspiration time.

2. A ventilator according to claim 1, wherein the processing unit is configured to shorten the expiratory time if the current end-expiratory gas flow is below the lower threshold value.

3. A ventilator according to claim 1, wherein the processing unit provides a time control in which the current end-expiratory gas flow acts as a measured variable of the time control and the inspiration time acts as a manipulated control variable of the time control, and wherein the lower threshold value represents a target value of the measured variable.

4. A ventilator according to claim 1, wherein the processing unit is configured to extend the expiratory time if the current end-expiratory gas flow is above the upper threshold value.

5. A ventilator according to claim 1, wherein the lower threshold value or the upper threshold value or both the lower threshold value and the upper threshold value are dependent on the measured course profile of the gas flow-dependent measured values.

6. A ventilator according to claim 5, wherein the lower threshold value or the upper threshold value or both the lower threshold value and the upper threshold value are dependent on a maximum expiratory gas flow during the expiratory time of the provided ventilation, determined from the gas flow-dependent measured values.

7. A ventilator according to claim 1, wherein the processing unit is further configured to reduce the increase in gas pressure at the beginning of the inspiration time or to reduce the maximum pressure of the breathing gas or both to reduce the increase in gas pressure at the beginning of the inspiration time and to reduce the maximum pressure of the breathing gas, if the inspiration time is lengthened.

8. A ventilator according to claim 1, wherein the processing unit is further configured to determine a current end-inspiratory gas flow via the course profile of the gas flow-dependent measured values and, depending on the current end-inspiratory gas flow, to adjust a ramp duration of an increase of the gas pressure of the breathing gas at the beginning of the inspiration time.

9. A ventilator according to claim 8, wherein the processing unit is configured to extend the ramp duration if the current end-inspiratory gas flow is below a lower inspiratory threshold value, and also shorten a remaining plateau duration of the inspiratory time such that the inspiratory time is independent of the end-inspiratory gas flow.

10. A ventilator according to claim 8, wherein the processing unit provides a ramp control in which the current end-inspiratory gas flow acts as a measured variable of the ramp control and the ramp duration acts as a manipulated control variable of the ramp control, and wherein the lower inspiratory threshold represents a target value of the measured variable.

11. A ventilator according to claim 8, wherein the processing unit is configured to shorten the ramp duration if the current end-inspiratory gas flow is above an upper inspiratory threshold value, and to also extend a remaining plateau duration of the inspiratory time such that the inspiratory time is independent of the end-inspiratory gas flow.

12. A ventilator according to claim 1, wherein the processing unit is further configured to extend the expiration time or to extend a ramp duration of an increase of the gas pressure of the breathing gas at the beginning of the inspiration time or to extend the expiration time and to extend a ramp duration of an increase of the gas pressure of the breathing gas at the beginning of the inspiration time at constant maximum pressure only if thereby a mean ventilation pressure over the corresponding breathing cycle is not below a predetermined lower mean pressure threshold value.

13. A process of operating a ventilator to mechanically ventilate a patient, the process comprising the steps of:

measuring a course profile of gas flow-dependent measured values in a ventilation circuit of the ventilator and outputting a corresponding sensor signal;

storing a plurality of ventilation parameters of a currently provided ventilation mode, said stored ventilation parameters indicating at least an inspiration time of the currently provided ventilation mode by the ventilator and a subsequent expiration time for a corresponding breathing cycle;

receiving the sensor signal and determining at least one current end-expiratory gas flow based on the course profile of the gas flow-dependent measured values; and adjusting a ratio between the inspiration time and the expiration time for the currently provided ventilation mode for ventilating the patient depending on a comparison between the determined current end expiratory gas flow and a lower threshold value or an upper threshold value or both a lower threshold value and an upper threshold value, wherein a duration of the corresponding breathing cycle remains essentially constant, wherein, depending on the adjustment of the inspiration time, an increase of a gas pressure of the breathing gas is adjusted at the beginning of the inspiration time or a maximum pressure of the breathing gas is adjusted during the inspiration time or both an increase of a gas pressure of the breathing gas is adjusted at the beginning of the inspiration time and a maximum pressure of the breathing gas is adjusted during the inspiration time.

14. A process in accordance with claim 13, wherein the lower threshold value or the upper threshold value or both the lower threshold value and the upper threshold value are dependent on a maximum expiratory gas flow during the expiratory time of the provided ventilation, determined from the gas flow-dependent measured values.

15. A process in accordance with claim 13, wherein the lower threshold value is between 0.1% and 5% of a maximum expiratory gas flow.

16. A process in accordance with claim 13, wherein the lower threshold value is 2% of a maximum expiratory gas flow.

17. A ventilator according to claim 1, wherein the lower threshold value is between 0.1% and 5% of a maximum expiratory gas flow.

18. A ventilator according to claim 1, wherein the lower threshold value is 2% of a maximum expiratory gas flow.

\* \* \* \* \*